United States Patent [19]

Greer et al.

[11] Patent Number: 5,005,578

[45] Date of Patent: Apr. 9, 1991

[54] THREE-DIMENSIONAL MAGNETIC RESONANCE IMAGE DISTORTION CORRECTION METHOD AND SYSTEM

[75] Inventors: Douglas S. Greer; Alan S. Gevins, both of San Francisco, Calif.

[73] Assignee: SAM Technology, Inc., San Francisco, Calif.

[21] Appl. No.: 329,792

[22] Filed: Mar. 28, 1989

Related U.S. Application Data

[63] Continuation-in-part of Ser. No. 287,138, Dec. 21, 1988, abandoned, which is a continuation-in-part of Ser. No. 177,681, Apr. 5, 1988, abandoned, which is a continuation-in-part of Ser. No. 942,204, Dec. 16, 1986, Pat. No. 4,736,751.

[51] Int. Cl.$^5$ ............................................. A61B 5/055
[52] U.S. Cl. .................................. 128/653 A; 324/318
[58] Field of Search .................. 128/653 A; 324/300, 324/308, 312, 318

[56] References Cited

U.S. PATENT DOCUMENTS

| 4,551,678 | 11/1985 | Morgan et al. | 324/300 |
| 4,583,538 | 4/1986 | Onik et al. | 128/653 |
| 4,625,168 | 11/1986 | Meyer et al. | 324/308 |
| 4,774,468 | 9/1988 | Bydder | 324/318 |
| 4,816,762 | 3/1989 | Bohning | 324/300 |
| 4,857,847 | 8/1989 | Machida | 324/312 |

*Primary Examiner*—Kyle L. Howell
*Assistant Examiner*—Krista M. Pfaffle
*Attorney, Agent, or Firm*—Eliot S. Gerber

[57] ABSTRACT

A method and system in Nuclear Magnetic Resonance (NMR) medical imaging systems corrects for three-dimensional distortions arising from the apparatus and patient specific distortions using a phantom and a helmet, both of which have fiducial markers in a three-dimensional matrix. The positions of the phantom and helmet fiducial markers are automatically detected and compared in a computer system which uses image transform algorithms to correct for the various distortions.

4 Claims, 4 Drawing Sheets

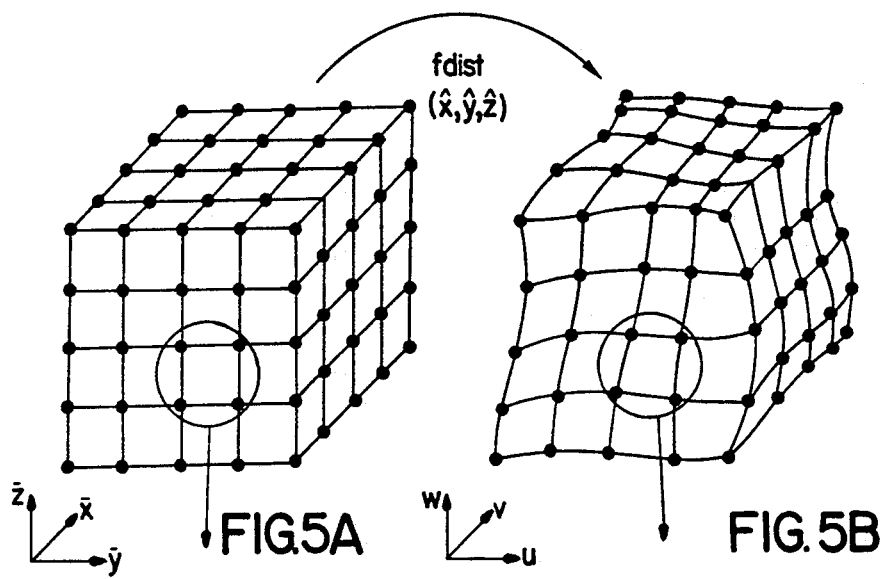
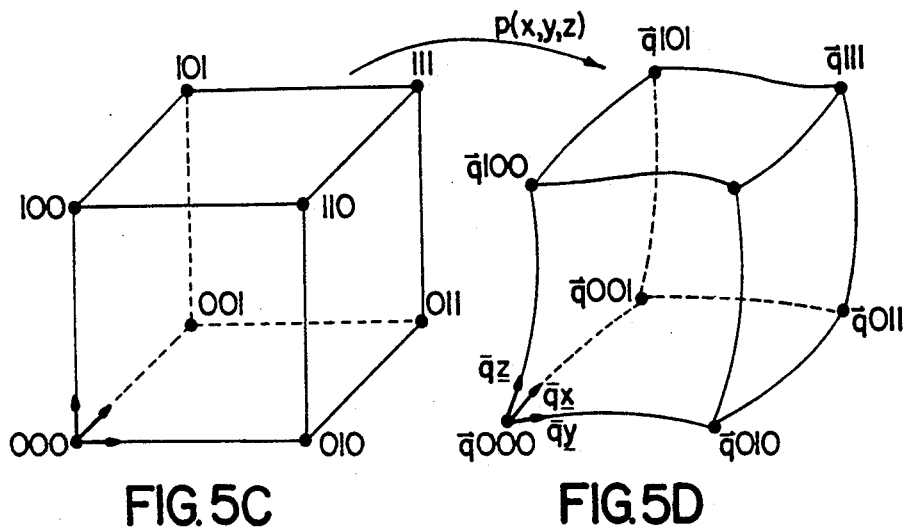
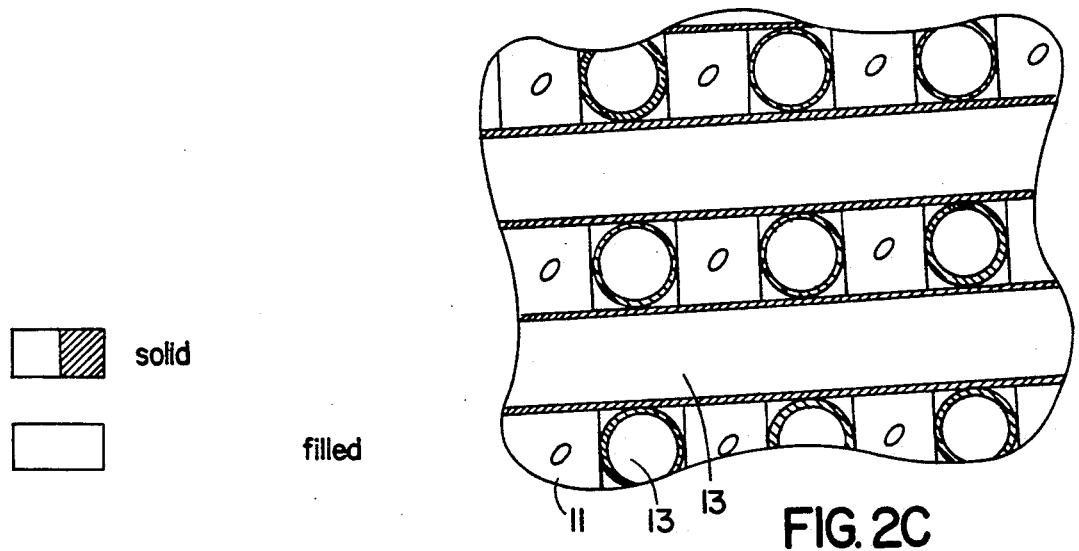

THREE-DIMENSIONAL MAGNETIC RESONANCE IMAGE DISTORTION CORRECTION METHOD AND SYSTEM

CROSS-REFERENCES TO RELATED APPLICATIONS

This application is a continuation-in-part based upon Ser. No. 287,138, filed Dec. 21, 1988, now abandon which was a continuation-in-part based upon Ser. No. 177,681, filed Apr. 5, 1988, now abandoned, which was a continuation-in-part based on Ser. No. 942,204, filed Dec. 16, 1986, now U.S. Pat. No. 736,751, issued Apr. 12, 1988.

BACKGROUND OF THE INVENTION

1. Field of the Invention

The present invention relates to in-vivo human subject medical imaging systems using Nuclear Magnetic Resonance (NMR) three-dimensional imaging and more particularly to the correction of distortion errors in NMR systems.

2. Related Art

In Nuclear Magnetic Resonance (NMR) or (MR) a strong magnetic field is applied across a subject and precisely pulsed radio frequency radiation waves are also applied. An atomic nucleus, for example, an atom of a portion of the human brain, as a result of its spin, has slightly different energy values. The nucleus absorbs the radio-frequency radiation and changes its energy value. That change is detected by a coil.

In one type of NMR system a steady (static) uniform magnetic field is applied in one plane and a linear gradient magnetic field is applied perpendicular (orthogonal) to the steady field. The gradient field is turned (rotated) about an axis. Three-dimensional data is obtained, processed by a computer system and used to produce a set of images representing slices of the body taken in various directions.

NMR imaging permits patients to be diagnosed without an invasive surgical procedure such as biopsy. It does not use X-rays, as in a CT scan, which may be harmful and yet permits a series of images to be taken over time.

While Magnetic Resonance (MR) images are invaluable because of their high degree of anatomical differentiation and their lack of ionizing radiation, they contain an inherent distortion which can exceed ten percent. The distortion arises from a number of sources including magnetic field inhomogeneities and patient-specific factors.

A series of articles has examined various aspects of the distortion problem. The articles are cited herein by their first author and year and the full citation is given at the end in the section entitled "Literature Cited". These articles, and the patents cited below, are incorporated by reference at the place of their citation. The articles relating to the distortion problem are: Lai, 1982; Crooks, 1984; Bendel, 1985; Pykett, 1983; Manassen, 1985; Sekihara et al, 1984; Sekihara et al, 1985b; Shenberg & Macovsky, 1985a; Feinberg, 1985; Hutchison et al., 1984. Although the existence of this distortion has not been well documented by MR device manufacturers, without distortion compensation, quantitative MR measurements, regarding position, length, area and volume, are likely to be erroneous.

The distortion can be classified as subject dependent or subject independent Subject independent distortion arises mainly from magnetic field inhomogeneity and calibration error which remains the same from patient to patient. It can therefore be measured and corrected from images of a phantom of known dimensions. Subject-dependent distortion changes with the chemical makeup and geometry of the subject being scanned, and is particularly difficult to detect and remove.

In U.S. Pat. No. 4,425,547 entitled "Nuclear Magnetic Resonance Apparatus Having Means For Compensating a Projecting Signal", a pair of standard signal sources of a specified atomic nucleus is positioned in a NMR device, around a body to compensate a projection signal.

U.S. Pat. No. 4,672,320 entitled "Imaging Apparatus and Method Using Nuclear Magnetic Resonance" describes a direct Fourier imaging system providing compensation for distortion caused by (i) changes in intensity of the static magnetic field from a predetermined standard and (ii) changes in intensity of the gradient magnetic field from a different predetermined standard. The system uses a computer-based system for such compensation and a small probe having a signal detecting coil.

U.S. Pat. No. 4,300,096 entitled "Imaging Systems", in a NMR device, the magnetic fields at a plurality of positions in the plane of a slice are measured to provide error signals used to adjust the gradient and orthogonal magnetic fields.

OBJECTIVES OF THE INVENTION

It is an objective of the present invention to provide an automatic computerbased system and method for the three-dimensional correction of distortions in Nuclear Magnetic Resonance (NMR) imaging systems which will correct for apparatus distortions and subject dependent distortions.

It is a further objective of the present invention to provide such a distortion correction system and method which may be readily and rapidly used with each patient.

BRIEF DESCRIPTION OF THE DRAWINGS

Other objectives of the present invention will be apparent from the following detailed description taken in conjunction with the accompanying drawings. In the drawings:

FIG. 2C is a side cross-sectional view showing one layer of the phantom of FIG. 2A;

FIG. 5A is a perspective view showing a block of the phantom and the locations of the fiducial markers;

FIG. 5B is a view similar to that of FIG. 5A but showing how the fiducial markers appear in the distorted image;

FIG. 5C is a perspective view of a single cube of fiducial locations;

FIG. 5D is a perspective view of a single hyperpatch (distorted image of the cube of FIG. 5C)

SUMMARY OF THE INVENTION

The present invention uses image transformation for removing the distortion. The principal issure of how to correctly resample the image data to undo the measured distortion is in theory given in the frequency domain by the two dimensional sampling theorem. However, the problem is confounded by nonlinear distortion and the additional effect on signal intensity caused by non-uniform gradient fields. Therefore both the image intensity and its position must be corrected.

Two hardware items are used for automatic distortion measurement and correction:

(1) a phantom with fiducial markers used to estimate the distortion characteristics of each NMR scanner, for example, each day; and (2) a helmet also with fiducial markers which is scanned along with each human subject to provide some degree of subject-dependent correction and to verify the distortion correction.

Figure 1A:
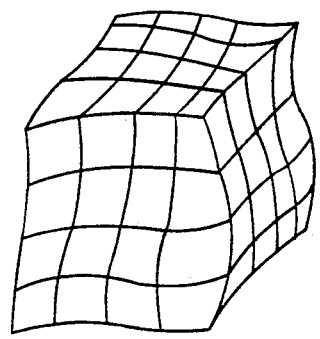
FIG. 1A is a three-dimensional perspective representation of the distorted MR (highly simplified) and FIG. 1B is a three-dimensional perspective representation of the corrected MR after distortion correction and resampling of the images.
Figure 1B:
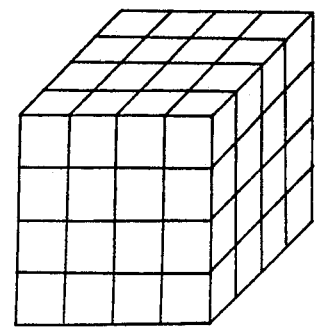

Automated measurement and correction of distortion, in the present invention, uses the same type and placement of fiducial markers in both the phantom and the helmet, which may be localized in the MRIs using simple statistical pattern-recognition algorithms. The differences between the location of each fiducial marker in the MR images and its actual location in the phantom is then used by a computational procedure to estimate the three-dimensional distortion function for all positions in the scanner. This distortion function allows for correction of the same distortion in other objects subsequently scanned (FIG. 1). For objects such as the human head, some additional distortion is usually present due to such causes as differences in magnetic susceptibility and differential chemical shift. Correction using the additional fiducial markers in the helmet worn by the subject removes some of the subject-dependent distortion. The residual subject-dependent distortion is countered with another software technique which maximizes the similarity of the corresponding MR intensity for locations in two orthogonal planes at their line of intersection.

The 3-D distortion measurement and correction system and method is comprised of:

(1) a phantom and a helmet with fiducial markers to be worn by patients in the scanner;

(2) algorithms for distortion assessment and correction; and (3) machine-independent software modules which assess and correct distortion, and which facilitate examination, manipulation and quantitative measurement of MR images.

Although the system was developed to correct MR distortion, it can also be directly applied in repositioning serial recordings made over an extended period of treatment and aligning MRs with CT, PET and SPECT images. All of these have direct application in research and clinical practice.

DETAILED DESCRIPTION OF THE INVENTION

Phantom: As shown in FIGS. 2A–3B, the distortion correction requires a large number of regularly spaced, easily recognized fiducial markers. Since standard phantoms are lacking in this regard, there is provided a custom phantom 10 with a dense, uniform matrix of special fiducial markers 11. Also, since standard phantoms are too small to allow measurement of field inhomogeneities at the edges of the field, the phantom is larger.

Figure 2A:
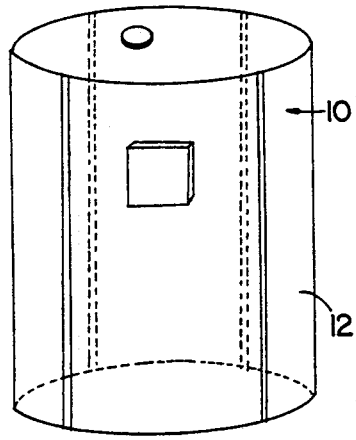
FIGS. 2A and 2B show the phantom of the present invention used for automatic recognition of fiducial markers, with FIG. 2A being a perspective view of the entire phantom and FIG. 2B being an enlarged perspective internal view of a portion of the phantom of FIG. 2A.

The outer shell 12 of the phantom 10 is an acrylic cylindrical tank, 26 cm in diameter and 30 cm in length (FIG. 2A). This size will fit all the commercial scanners. It has four posts on the inner walls for strength and which also function to hold the inner construction in place. Acrylic sheets form the top and bottom. There is a hole for filling and emptying copper sulfate solution or other fluid medium.

Figure 2B:
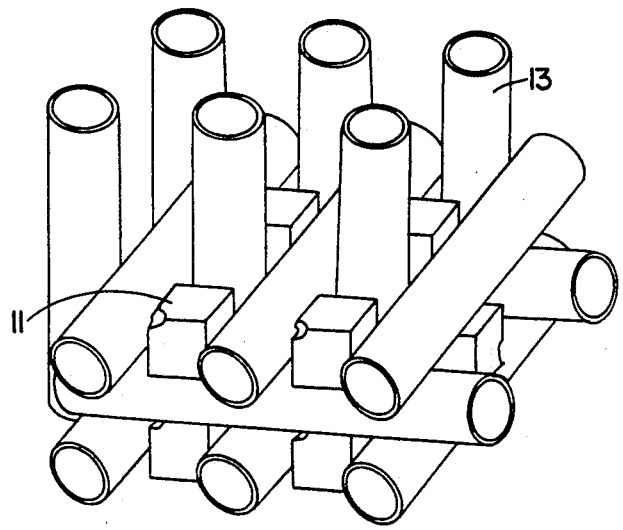

The inside construction consists of a three-dimensional lattice of hollow acrylic tubes 13, 1 cm in diameter, closely packed in three orthogonal planes. Solid cubes 11, 1 cm on each side, with a hole drilled through opposite corners, are positioned into the available spaces between the tubes, which act to rigidly maintain the regular spacing of the cubes. FIG. 2b shows a perspective view of a small portion of this construction. A planar cross-section is shown in FIG. 2c. The hole drilled through each cube is in the same orientation for all cubes in the phantom and helmet. The angle this hole makes with respect to the MR image in the x-y plane is approximately 35.2 degrees. In the image this hole appears as an ellipse with a major axis length of about 0.43 cm and a minor axis of about 0.25 cm. The component of the distortion function perpendicular to the image plane, i.e, the z position of the image, is then determined from the location of this ellipse in the image. When the tank is otherwise completely filled with solution the acrylic shows good contrast in MR images, and the simpler planar configuration allows for the straight-forward algorithmic determination of location within the phantom. A measurement code is embossed on the surface of the tank to facilitate repositioning the phantom for repeated measurements to verify the correct location of the internal structure.

Figure 3A:
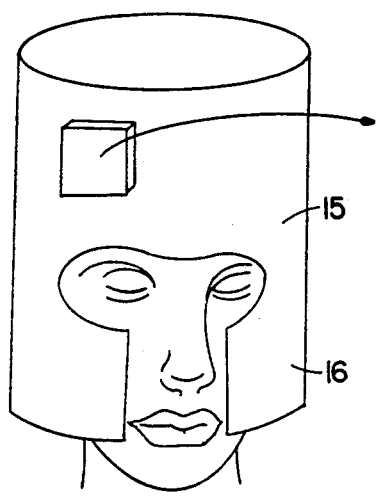
FIG. 3A is a perspective view of the helmet of the present invention.
Figure 3B:
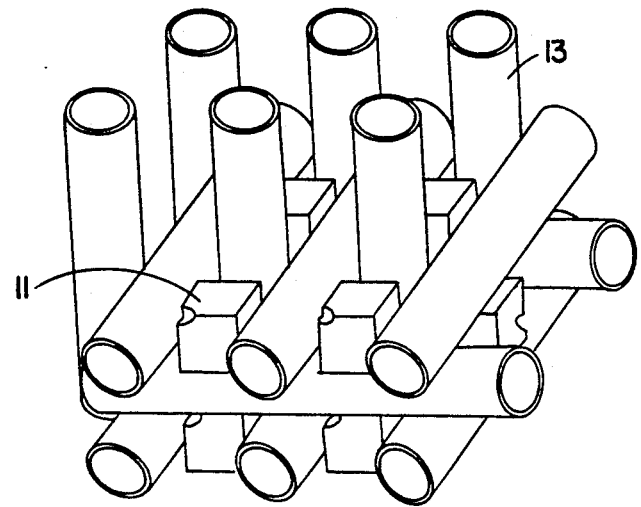
FIG. 3B is an enlarged internal perspective view of a portion of the helmet of FIG. 3A.

The special calibration helmet 15 is made from the same materials and construction of the phantom described above. The outside is a similar acrylic tank 16 (FIG. 3A). The inside is made of the same tube-and-cube construction, hollowed-out to accommodate the shape of a human head (FIG. 3b). The side of the cylinder is cut away to expose the subject's mouth, nose and eyes. Another two holes at either side expose the subject's ears. A heated thermoplastic is molded to conform to the inside of the helmet and is cemented in place to form a water-tight seal. The helmet is filled with solution through a fill hole (not shown). A system for measuring the exact position of the subject's head within the helmet using a pair of perpendicular ruled scales is positioned over the nasion and also over the preauricular notches of both ears (not shown).

For the subject's comfort and also for accurate positioning of the subject's head in the helmet, various sizes of foam inserts are used to fit various head sizes.

Software: The three main software components are: (1) automated recognition of fiducial markers in MRIs of the phantom and the helmet; (2) distortion correction with a 3-D spline-fitting algorithm which uses all the distortion measurements made with the phantom data; and (3) an orthogonal plane alignment algorithm which corrects remaining subject-dependent distortion.

(1) Automatic Recognition of Fiducials

The tubes and cubes constitute fiducial markers whose arrangement is designed so that their cross section in different plane orientations has a known unique shape and intensity profile. Recognition of their locations in the MR images is done by template matching using matched filters (Duda, 1973). This method allows optimal detection of a known signal in the presence of white Gaussian noise (Helstrom, 1975).

A histogram equalization technique over the region of the phantom is used to make the fiducial markers more easily recognized. The phantom calibration images contain MR data of three principal materials: air, acrylic and a liquid filler, usually copper sulfate solution. The center portion of the MR images contains only solution and the acrylic tubes and cubes. The first step is to form a histogram of the image signal intensity over a 10 cm. cube near the center of the phantom. If any MRI data is acquired with only one average, the images are filtered with as 3×3, Gaussian weighted finite impulse response filter before the histogram computation in order to reduce noise.

Many of the voxels contain some solution and some plastic. However, when the voxel dimensions are much smaller than the outside dimension of the cubes, the maximum and minimum values in the histogram correspond to voxels that contain only solution and acrylic, respectively. The intensity values corresponding to 1-2 and the 98-99 percentiles in the histogram intensity profile provide approximate values for the pure acrylic and solution signal. Using these two values the approximate ratio of the two materials in any voxel of the phantom is determined. The grey level equal to the average of the estimated solution and acrylic signal values corresponds to voxels containing 50% solution and 50% acrylic and is used to determine the boundaries of the fiducial markers. Using the 50% grey level value as a threshold value, the cube and in-plane tube boundaries are then determined.

Figure 4:
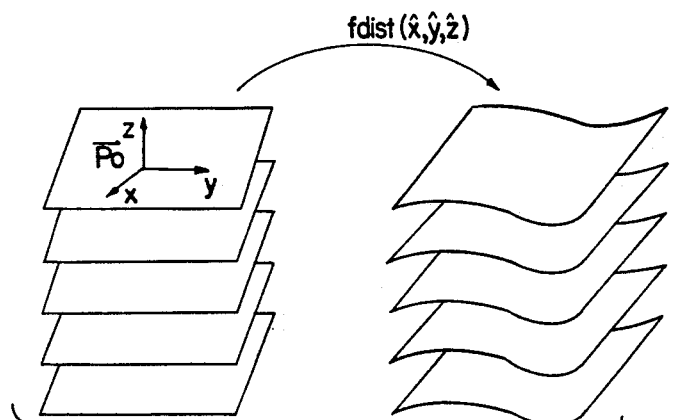
FIGS. 4, 4A and 4B illustrate the MR distortion function showing coordinate systems for translating between the nominal (apparent) locations of the image and the undistorted (true locations)
Figure 4A:
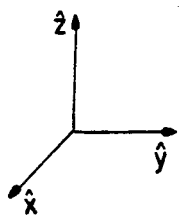
Figure 4B:
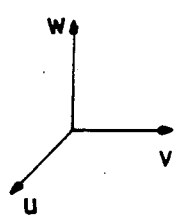

Assume for this discussion that the image is in the X, Y plane and is therefore perpendicular to the Z axis. Using a matched filter with a pattern equal to a cross section of the acrylic tubes, the locations of the tubes running in the Z direction can be found. These locations form a checkerboard over the image and are used to determine the X and Y components of the distortion. The Z component of the distortion is calculated by examining the position of the elliptical cross section of the cylindrical hole running through the cubes. (2) Distortion Characterization The distortion is quantified using a distortion function which maps from the image space into the actual spatial position inside the magnet. An example of this distortion function is illustrated in FIG. 4. The image space is parameterized by coordinates u, v and w that identify locations in the acquired MR image data. The true physical location is parameterized with the usual Cartesian coordinates x, y, and z. Also shown in FIG. 4 is a local coordinate system x, y, and z which is translated by $P_0$ from the fixed reference frame. Parameter values for voxel size, image location and orientation, contained in the MR computer data files, indicate the nominal voxel location. However, due to distortion the true voxel location (the actual position of the tissue which generated the signal for that voxel) is displaced from its nominal location. The function describing the displacement is the position distortion function $f_{dist}(x, y, z)$ We have defined the image space coordinates in such a way that for error free MR image the distortion function is just the identity function which in vector notation is:

$$I(x,y,z) = (u,v,w) \quad (1)$$

i.e., $$I_x(x,y,z) = u$$

$$I_y(x,y,z) = v$$

$$I_z(x,y,z) = w$$

We define the distortion function $f_d$ as the error in displacement which is $$f_d(x,y,z) = f_{dist}(x,y,z) - I(x,y,z) \quad (2)$$

The successful result of the distortion removal process is a set of images that have the displacement equal to the identity function or $$f_d(x,y,z) \equiv 0$$

In terms of correcting for distortion, the component of the error which remains constant independent of the object being imaged is referred to as subject independent. The error which changes based on the object imaged is referred to as subject dependent. The method of analysis and correction of these two types of distortion is fundamentally different. Accordingly, the distortion is decomposed into the subject dependent part $f_{sd}(x, y, z)$ and subject independent part $f_{si}(x, y, z)$. The total distortion is then:

$$f_d(x,y,z) = f_{sd}(x,y,z) + f_{si}(x,y,z) \quad (3)$$

(a) Subject-Independent Distortion.

The primary source of subject independent distortion is the image warping due to inhomogeneities in the gradient magnetic field. This distortion can be accurately measured using the phantom or estimated from the fiducial helmet worn by the patient. In either case, a volume spline is calculated and used to remove this component of the distortion.

A set of reference points is obtained from the images of the phantom or of the fiducial helmet worn by the patient. The true physical location of these points is known from its construction. By locating their position in the images, the distortion function at these reference positions can be calculated precisely. For the phantom, these reference points provide about 1600 points where the distortion is exactly known. The locations of the reference points in the images is determined automatically as described above. A smooth three-dimensional, volume spline function that passes through these reference points is computed and used to estimate and correct the distortion in the space between the known locations. Interpolating splines which pass through the reference points are used since the estimated distortion function should correspond exactly at the known reference locations.

The subject independent distortion function is a volume spline over the entire image space and is composed of a number of so-called "hyperpatches" (Mortenson, 1985; Faux, 1981). The number of hyperpatches used to construct the complete distortion function is based on the number of known reference locations that are determined from the phantom data or calibration helmet (FIG. 5). Splines where each coordinate function is locally a cubic polynomial are used because they are well behaved, have the appropriate number of degrees of freedom and can be computed easily and accuratedly. The hyperpatch coefficients are computed locally over a small number of reference points and "patched" together to form the complete distortion function in a way that ensures that the partial derivatives are continuous at the patch boundaries. The more hyperpatches used, the greater the overall accuracy and required computation time. To make the notation simpler we use the local coordinate system translated by $p_o$ so that $$(x,y,z) = (x,y,z) - (p_{0x}, p_{0y}, p_{0z})$$

Each hyperpatch is a cubic polynomial in three variables of the form:

$$p(x,y,z) = \sum_{i=0}^{3} \sum_{j=0}^{3} \sum_{k=0}^{3} a_{ijk} x^i y^j z^k \quad (4)$$

The $p(x,y,z)$ is local estimate of the distortion function expressed in terms of the algebraic coefficients $a_{ijk}$. The p and a are vector variables which are broken into their u, v and w components. For the above equation the u components is:

$$p_x(x,y,z) = a_{333u} x^3 y^3 z^3 + a_{332u} x^3 y^3 z^2 + a_{331u} x^3 y^3 z + a_{330u} x^3 y^3 +$$
$$a_{323u} x^3 y^2 z^3 + a_{322u} x^3 y^2 z^2 + a_{321u} x^3 y^2 z + a_{320u} x^3 y^2 +$$
$$\vdots$$
$$a_{003u} z^3 + a_{002u} z^2 + a_{001u} z + a_{000u}$$

There are consequently 64 coefficients for each of 3 dimensions for a total of 192 for each hyperpatch. These are computed from the known reference locations as follows:

The phantom calibration points are at unit intervals throughout a volume and the composite distortion function is decomposed into hyperpatchs so that each hyperpatch maps the volume of a cube in the phantom into a distorted cube. The eight corners of this distorted cube are the measured image locations $q_{000}$, $q_{001}$, $q_{010}$, $q_{011}$, $q_{100}$, $q_{101}$, $q_{110}$ and $q_{111}$. The three digit subscript on each q corresponds to the x, y and z coordinate of the unit cube.

The algebraic coefficients are computed from the equation:

$$a_{ijk} = \sum_{l=0}^{4} \sum_{m=0}^{4} \sum_{n=0}^{4} m_{il} m_{jm} m_{kn} b_{lmn} \quad (5)$$

The $b_{lmn}$, which are explicitly given below, are called the geometric coefficients and are equal to the reference points and the estimated partial derivatives across the patch boundaries. The $m_{ij}$ are coefficients of the transformation matrix M given by:

$$M \equiv [m_{ij}] = \begin{bmatrix} 2 & -2 & 1 & 1 \\ -3 & 3 & -2 & -1 \\ 0 & 0 & 1 & 0 \\ 1 & 0 & 0 & 0 \end{bmatrix} \quad (6)$$

A x, y and z superscripts on the q vectors is used to denote partial differentiation with respect to that variable. An estimate of their value is the average of the differences between adjacent reference point locations. By equating these on neighboring patchs, the spline is "smooth" in the sense that it is continuous and has continuous partial derivatives. A each corner there are three tangent vectors, three twist vectors and a triple mixed partial. For the corner (x=1, y=1, z=0) these are:

$q_{110} \equiv$ corner point $q^x_{110}, q^y_{110}, q^z_{110} \equiv$ tangent vectors $\frac{\partial}{\partial z}, \frac{\partial}{\partial y}, \frac{\partial}{\partial z}$ $q^{xy}_{110}, q^{xz}_{110}, q^{yz}_{110} \equiv$ twist vectors $\frac{\partial^2}{\partial x \partial y}, \frac{\partial^2}{\partial x \partial z}, \frac{\partial^2}{\partial y \partial z}$ $q^{xyz}_{110} \equiv$ triple mixed partial $\frac{\partial^3}{\partial x \partial y \partial z}$ The geometric coefficients $b_{ijk}$ are a three dimensional array of vectors. This three dimensional "cube" or tensor of vectors can be divided into four matrices where each matrix is 4 by 4 square. These can be written out as:

$$[b_{ij1}] = \begin{bmatrix} q_{000} & q_{010} & q^y_{000} & q^y_{010} \\ q_{100} & q_{110} & q^y_{100} & q^y_{110} \\ q^x_{000} & q^x_{010} & q^{xy}_{000} & q^{xy}_{010} \\ q^x_{100} & q^x_{110} & q^{xy}_{100} & q^{xy}_{110} \end{bmatrix}$$

$$[b_{ij2}] = \begin{bmatrix} q_{001} & q_{011} & q^y_{001} & q^y_{011} \\ q_{101} & q_{111} & q^y_{101} & q^y_{111} \\ q^x_{001} & q^x_{011} & q^{xy}_{001} & q^{xy}_{011} \\ q^x_{101} & q^x_{111} & q^{xy}_{101} & q^{xy}_{111} \end{bmatrix}$$

$$[b_{ij3}] = \begin{bmatrix} q^z_{000} & q^z_{010} & q^{yz}_{000} & q^{yz}_{010} \\ q^z_{100} & q^z_{110} & q^{yz}_{100} & q^{yz}_{110} \\ q^{xz}_{000} & q^{xz}_{010} & q^{xyz}_{000} & q^{xyz}_{010} \\ q^{xz}_{100} & q^{xz}_{110} & q^{xyz}_{100} & q^{xyz}_{110} \end{bmatrix}$$

$$[b_{ij4}] = \begin{bmatrix} q^z_{001} & q^z_{011} & q^{yz}_{001} & q^{yz}_{011} \\ q^z_{101} & q^z_{111} & q^{yz}_{101} & q^{yz}_{111} \\ q^{xz}_{001} & q^{xz}_{011} & q^{xyz}_{001} & q^{xyz}_{011} \\ q^{xz}_{101} & q^{xz}_{111} & q^{xyz}_{101} & q^{xyz}_{111} \end{bmatrix}$$

Equation (4) is invertible. Consequently the equivalent geometric coefficients can be calculated even when a more complex method is used to calculate the algebraic coefficients.

Both the algebraic and geometric coefficients have intuitive interpretations. This is illustrated by examining the situation when there is little or no distortion. In this case the $q_{xyz}$ are the true positions of the eight corners of each cube. The tangent vectors $q_{xyz}^x$, $q_{xyz}^y$ and $q_{xyz}^z$ are the unit vectors $(\pm 1,0,0)$, $(0,\pm 1,0)$ and $(0,0,\pm 1)$ respectively. The twist and triple mixed partial vectors are zero. In the absence of distortion the algebraic coefficients are zero except for $a_{000}$ which is one of the cube corners and $a_{100}$, $a_{010}$ and $a_{001}$ which are also the unit vectors $(\pm 1,0,0)$, $(0,\pm 1,0)$ and $(0,0,\pm 1)$ respectively.

Variations of the coefficients from the distortionless values provide a quantitative as well a qualitative measure of the extent and character of the distortion error.

(b) Subject-Dependent Distortion.

There are two methods for correcting subject-dependent distortion. The first method requries an estimate of the differential effects of variations in tissue composition on the magnetic field gradient. The second method is a purely computational approach which is based upon redundant information contained in the MR images. In the former method, direct or indirect estimates of tissue composition effects are obtained. A subject-dependent shift map S(x,y,z) is then made which corresponds pixel to pixel with the image data. Let $M_0(x,y,z,t)$ denote the gradient field and let H(t) denote the RF pulse in the rotating frame. The subject-dependent distortion is a function of the main and gradient field strength, the RF pulse, and the shift map.

$$f_{sd}(x,y,z) = F(B_0, M(x,y,z,t), H(t), S(x,y,z)) \quad (7)$$

Combining this with the subject-independent distortion yields the total distortion function $f_d(x,y,z)$ used to generate the corrected images.

(3) Distortion Correction a. General Method

Once the distortion measurement and characterization is complete, a corrected set of images are produced. This process can be viewed as a rescanning or resampling procedure.

The theoretical basis for the rescanning procedure is the sampling theorem describing the relationship between the continuous image and its discretely sampled representation (Oppenheim, 1975; Rabiner, 1975; Rosenfeld, 1976). The continuous image (image volume) is the convolution of a point spread function and a two (three) dimensional impulse function weighted by the pixel (voxel) values (Papoulis, 1972; Stockham, 1975; Pratt, 1975). Because neither the distortion function nor its inverse is linear, it maps the point spread function non-uniformly at different image locations. Since the point spread function is not linear shift-invariant, the usual frequency domain theorems are no longer valid, and the relationship between the frequency and space domain is not linear.

The situation is similar to that which arises in texture mapping and non-linear image warping (Blinn, 1976; Catmull, 1980; Andrews, 1979; Bier, 1986). The process is confounded by aliasing from a non-uniform point spread function. A number of efficient algorithms have been developed in the two dimensional case for dealing with this problem (Heckbert, 1986; Fant, 1986; Weiman, 1980). An extension of these methods to the three dimensional case is used in the distortion correction procedure.

The method for resampling involves systematic sampling through the corrected image space and using the distortion map $f_{dist}$ to index into the correct location in the distorted MR image data. This avoids having to explicitly calculate the inverse distortion function. The partial derivatives of the distortion function are used to determine an approximation to the point spread function. This approximation is used to calculate the weighted coefficients that are multiplied by the voxel values in a local neighborhood of the distorted image.

A problem that occurs in MR images is that not only is the image spatially distorted, but the image intensity is also erroneous. This occurs because the displayed intensity corresponds to the measured RF signal from a volume of tissue which changes in size due to the magnetic field distortion. If we merely sampled a point from the distorted image, we would have to correct for the intensity distortion by multiplying by a factor V. Where:

$$V = det \left| \partial \frac{f_{dist}}{\partial x}, \partial \frac{f_{dist}}{\partial y}, \partial \frac{f_{dist}}{\partial z} \right|$$

$$= f^x_{dist} \cdot f^y_{dist} \times f^z_{dist}$$

By using the appropriate point spread function, this correction becomes part of the anti-aliasing calculation.

The MR image headers contain information describing the image location parameters such as center of view, field of view, and pixel or voxel size. Usually, the new images are located in the same location as the distorted images. If there is a large amount of distortion and the interslice distance between images is large compared to the voxel size, it may be advantageous to choose new image locations. The new locations then correspond to a planar approximation of the distorted image location. This new location reduces the large interplanar interpolation between slices. This also prevents portions of the images from being shifted out of view without having to increase the number of image pixels. Since inter-image interpolation may cause some blurring if the interslice distance is large, it is best not to interpolate between images when there is a gap or "skip" between image slices; only within image distortion should be corrected.

In some applications, it is advantageous to move the image plane since the precise location is still known and the above procedure removes the non-planar distortion but uses less interslice interpolation. The system allows the operator to choose either image location option to suit his requirements.

b. Orthogonal Plane Alignment Procedure

The orthogonal plane method is useful for removing a large amount of subject dependent distortion without having first characterized magnetic susceptibilitiy and chemical shift effects.

Figure 6:
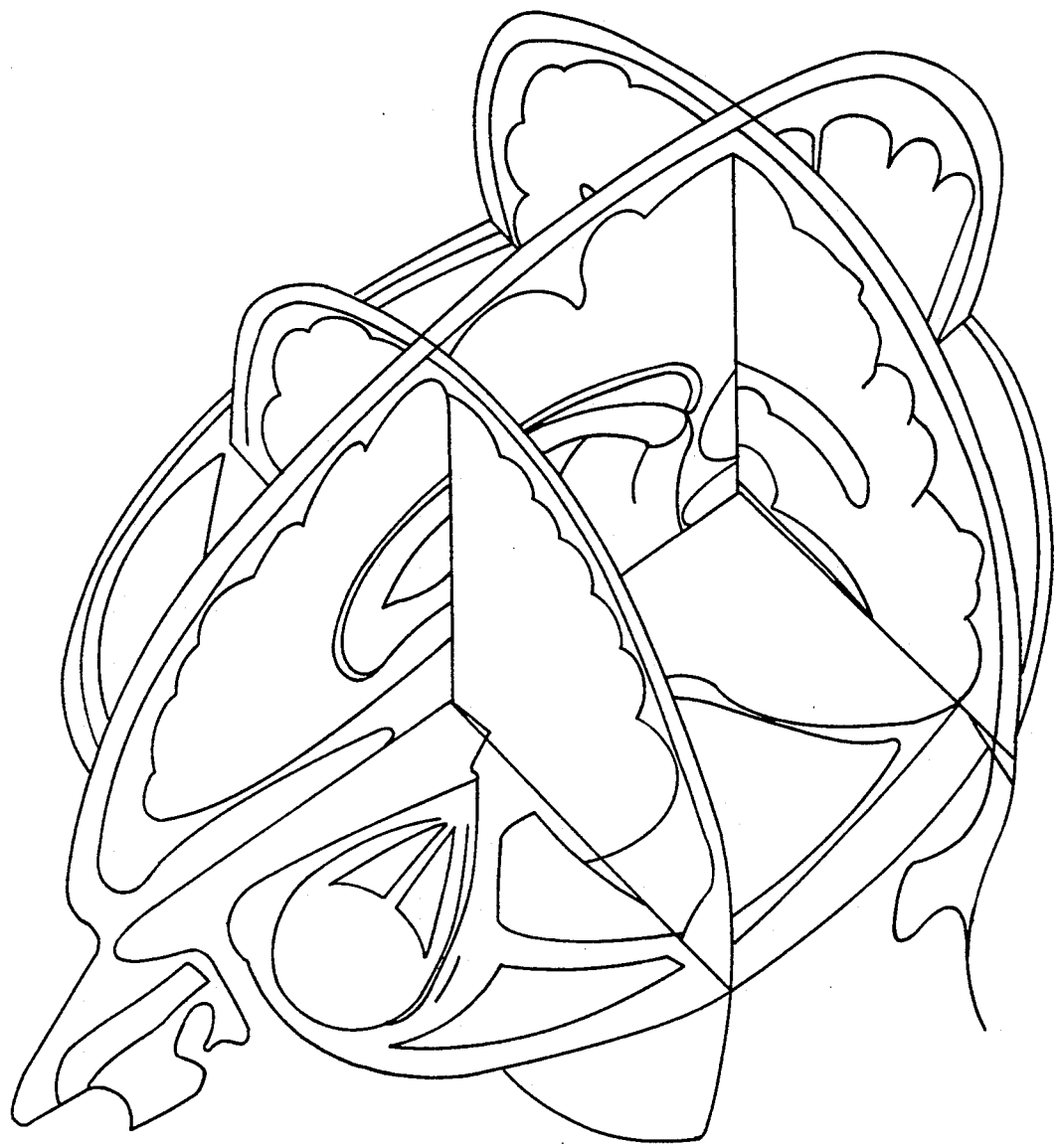
FIG. 6 is a perspective composite MR image in which sagittal, horizontal and coronal views are mathematically juxtaposed.

The rationale is as follows. The MR data in the coronal, axial and sagittal images is spatially redundant. Any two orthogonal planes such as axial and coronal intersect along a common line. These lines of intersection can be clearly seen in composite images such as FIG. 6. This redundant information is used to correct for some of the subject-dependent distortion, such as chemical shifts, in addition to the subject-independent corrections.

In the absence of distortion and calibration error, the pixel data along the line of intersection should be exactly equal. With distortion, the line becomes a curve describing the location of tissue common to both images. The orthogonal plane alignment method finds a distortion function such that removing the spatial and concomitant intensity error caused by this distortion function generates images with matching intensity values at their intersections.

A general formulation allows two arbitrarily different curves in each plane to be brought into alignment. After alignment, the image data is self consistent, but may vary from its true position. When the subject-independent distortion has been removed, several types of subject-dependent distortion (e.g. chemical shift and differences in magnetic susceptibility) result in a "symmetric" shift in any two orthogonal image planes. Consequently, the problem is greatly simplified since there is a single distortion shift function for both image planes. After alignment, the image data is in its true position, as well as being self consistent. The direction of the shift depends on the RF and field gradient pulse sequences. If this information is not available from the MR device manufacturer, it can be inferred from a phantom scan.

The fundamental problem is to calculate the required distortion function that brings the images into alignment. An iterative relaxation method is used to calculate the orthogonal plane distortion function (Marr, 1982):

$$C_{x,y}^{t+1} = \sigma \left\{ \sum_{a,\delta \in Y(x,y)} C_{a;\delta}^t - \rho \sum_{a,\delta \in X(x,y)} C_{a;\delta}^t \right\}$$

where $C_{a;\delta}^t$ describes how well the images match for line position a and distortion shift $\delta$ at interaction t. $Y(x,y)$ is the set of positions lateral to x,y and $X(x,y)$ are the positions in line with x,y. The Greek letter $\rho$ is an inhibitory constant and $\sigma$ is a threshold function. Initial values of the $C_{x,y}^0$ are set to all possible lateral distortion values. Multiple interactions cause a convergence to the best distortion "curve". Several variations of this basic form are possible that increase the rate of convergence (Dev, 1975; Harai, 1978; Marr & Poggio, 1976).

(4) Software Modules For Distortion Correction, and Quantitative Measurement of MR Images The system includes an extensive set of software tools which allows the user to interactively analyze, correct, and display MR image data in a 3-dimensional image processing and graphics computer workstation environment. The software tools allow data translation, graphical processing, distortion correction, 3-D reconstruction and image enhancement. A universal image format eliminates the need to rewrite the software for each type of MR scanner. Program modules translate data from each type of MR scanner into this format. This format is known as the Data Description Language (DDL) and consists of: (1) a header with textual information concerning the type, origin and characteristics of the data; and (2) the data itself which is usually stored in binary form. One class of DDL file is Image data which includes MR, Computed Tomography (CT) and Positron Emission Tomography (PET) scans, and conventional digitized X-ray images. To allow for three-dimensional reconstruction of MR, CT and PET images, the DDL header contains a standard specification of the transform in homogeneous coordinates which locates the image in space. This allows the spatial location of any image pixel to be computed by a simple multiplication of a 1×4 vector by a 4×4 matrix. Conversely, the pixel in a series of images which is nearest to any spatial position can be calculated by multiplication by the inverse of the matrix.

Since all image processing and graphics programs operate on data in the universal image format, data from any MR (or CT or PET) scanner can be incorporated into the system simply by writing a small conversion program. Relevant information including patient and hospital descriptions, image size and orientation, pulse sequence type, and basic parameters such as TR, TE and number of averages are extracted from the machine-specific binary image header and converted into human-readable text in the DDL file. Information available on only one machine is included as optional fields in the DDL header. Except for the lowest level routines for displaying text, drawing simple line segments, and transferring pixels to the hardware frame buffer, all graphics and image processing software was designed to be machine independent.

Composite images: Programs that interactively identify the exact location of any pixel in an MR image are basic to any distortion measurement. A more advanced tool, generation of composite images, builds upon this capability. This three-dimensional perspective computer graphics capability allows visual assessment of measurements and calculations. The composite image method allows several images, or sections of images, which are not necessarily co-planar, to be displayed together from any viewpoint. The calculations normally include a perspective transformation so they appear exactly as they would if they had been cut from MRI plates and pasted together at the correct positions and angles. The composite image method is useful in detecting and qualitatively assessing distortion, regardless of source.

Tools for Correcting Spatial Aliasing and Head Movement: In addition to linear and nonlinear distortion, other problems are often present in MRI data, in particular, spatial aliasing and the effects of head movement. Software to remove spatial aliasing is included in the system. Other tools correct for head movements during the recording, and variations in head repositioning in serial recordings, by computing the coefficients for a translation and orthonormal rotation based upon the relative position of the fiducial markers in any two of the three orthogonal planes.

Tools for Image Enhancement: Image processing techniques such as histogram equalization and homomorphic image filtering are incorporated into the system. Enhancement techniques have proven useful since important anatomical structures are often hidden or difficult to discern.

Tools for Combining MR Images With Other Data: Programs for spatial manipulation allow data to be input in one coordinate system, transformed by any combination of rotation, translation or scaling, and then output or displayed in another coordinate system. Such transforms are necessary for distortion correction, and also are needed to combine, analyze or compare information from dissimilar sources, i.e., CT and MR scans, and cranium measures. The transformations can be specified and combined with the command language interface, saved and restored, and modified by other programs. As the composite images are created, a model is formed of their actual location in space. These images can therefore be easily combined with data taken from other sources.

Software Tools for Measuring Specific Brain Areas and Surface Reconstruction: Software tools allow individual sections to be taken from an image, and then measured and superimposed in a composite image. Basic geometric measurements are included in the system, as are symbolic display file representations and manipulations of basic geometric shapes. These have been combined with other algorithms for reconstruction of objects from serial sections. Data obtained from all three directions significantly improves accuracy, especially where the surface to be reconstructed is almost parallel to one of the imaging planes.

We claim:

1. A method in nuclear magnetic resonance (NMR) for the correction of distortions in an NMR scanner, including the steps of:

(a) positioning a plurality of fiducial markers at selected locations on a helmet, said markers providing a readily determined distinctive image in an NMR scan;

(b) placing a phantom having a plurality of predetermined fiducial markers at selected locations therein in said NMR device and taking a scan of said phantom; and then removing said phantom from said device after taking the scan;

(c) placing the helmet on a subject within the NMR device and taking a scan of the helmeted subject;

(d) comparing the locations of the fiducial markers in the scans of the phantom and the helmeted subject by an automatic comparison using a computer system and pattern recognition algorithms;

(e) computing in the computer system a first set of distortion corrections providing three-dimensional corrections for the NMR scanner; and (f) applying said three-dimensional corrections to the NMR scanner to produce corrected NMR scan images.

2. A method as in claim 1 and including an additional step, to correct for human subject dependent distortions, of computing in the computer system a second set of distortion corrections by using the first set of distortion corrections and a three-dimensional orthogonal planes relaxation algorithm.

3. A method as in claim 1 and including the additional step of:

computing an additional set of distortion corrections, to correct for human subject dependant distortions, using an orthogonal alignment algorithm.

4. An NMR phantom adapted to be used to correct distortions in a nuclear magnetic resonance device, said NMR phantom being a helmet having a hollowed-out space having the size and shape of a human head and adapted to receive a human head therein wherein, the helmet comprises a three-dimensional matrix of rows and columns having evenly spaced fiducial markers in each row and column, the markers providing a readily determined image of their location in a scan by a NMR device.

* * * * *